United States Patent [19]

Sagar et al.

[11] Patent Number: 5,660,769
[45] Date of Patent: Aug. 26, 1997

[54] METHOD OF ENCAPSULATING SUBSTANCES IN BIOCAPSULES

[75] Inventors: Brian Frederick Sagar; Anthony John Grant Sagar; Samuel Gordon Graham, all of Stockport; Reginald Trevor Wragg, Tamworth, all of Great Britain

[73] Assignee: CPC International Inc., Englewood Cliffs, N.J.

[21] Appl. No.: 532,643

[22] PCT Filed: Mar. 30, 1994

[86] PCT No.: PCT/GB94/00667

§ 371 Date: Nov. 11, 1995

§ 102(e) Date: Nov. 11, 1995

[87] PCT Pub. No.: WO94/22572

PCT Pub. Date: Oct. 13, 1994

[30] Foreign Application Priority Data

Mar. 31, 1993 [GB] United Kingdom ............... 9306700

[51] Int. Cl.$^6$ ...................................... A61K 9/50
[52] U.S. Cl. .............. 264/4; 424/451; 435/243; 435/255.1; 428/402.2; 428/402.24
[58] Field of Search ............... 264/4; 428/402.2, 428/402.24; 435/243, 255.1; 424/451

[56] References Cited

U.S. PATENT DOCUMENTS

| B 498,208 | 4/1976 | Shank | 424/93 |
| 4,574,086 | 3/1986 | Shackelford | 426/62 |
| 4,696,863 | 9/1987 | Matsushita et al. | 428/402.2 |
| 4,948,586 | 8/1990 | Bohm et al. | 424/406 |
| 5,288,632 | 2/1994 | Pannell | 435/243 |
| 5,443,813 | 8/1995 | Hainfeld | 424/1.17 |
| 5,496,728 | 3/1996 | Hardy et al. | 435/255.1 |
| 5,521,089 | 5/1996 | Ishiguro et al. | 424/489 |

FOREIGN PATENT DOCUMENTS

| 0085805 | 8/1983 | European Pat. Off. |
| 2179528 | 11/1973 | France. |
| 2162147 | 1/1986 | United Kingdom. |
| 2234901 | 2/1991 | United Kingdom. |

Primary Examiner—Jeffrey C. Mullis
Attorney, Agent, or Firm—Brooks Haidt Haffner & Delahunty

[57] ABSTRACT

There is disclosed a method for encapsulating a substance in a biocapsule comprising passing a solution into the biocapsule, then effecting a change in the biocapsule/solution system such that the substance remains encapsulated while a solvent escapes.

19 Claims, No Drawings

METHOD OF ENCAPSULATING SUBSTANCES IN BIOCAPSULES

This invention relates to methods for encapsulating substances.

It is known to encapsulate various substances in microcapsules which occur naturally or which can otherwise be referred to as biocapsules. U.S. Pat. No. 4,696,863, GB-A-2 162 147 and EP-A-0 242 135 disclose bioencapsulation in such organisms as yeast cells (which may be used alive or dead), microfungi, bacteria and algae.

Difficulties are encountered when trying to encapsulate certain substances. GB-A-2 234 901 discloses a method for encapsulating water-insoluble substances which are, however, soluble in liquid ammonia, which is used as the carrier by which the substance is carried by diffusion into the cell.

It is now found that even some water-soluble substances cannot effectively be encapsulated using an aqueous solution, because the substances pass out of the capsule as easily as they are passed in, and the present invention provides a generalised method which can be used with such and other difficult-to-encapsulate substances.

The invention comprises a method for encapsulating a substance in a biocapsule comprising passing a solution into the biocapsule, then effecting a change in the biocapsule/solution system such that the substance remains encapsulated while a solvent escapes.

The change may comprise a physical change, which may involve an increase in solution concentration, at least as a proportion of solution saturation level, within the capsule. It may involve a decrease in solubility of the substance in the solution within the capsule, as by cooling, and the substance may precipitate from a saturated solution within the capsule.

The solvent may however evaporate from the capsule, leaving behind the substance.

The solution may swell the biocapsule sufficiently to pass through the capsule wall to enter the capsule, and the change may then comprise a reversal of the capsule swelling sufficient to trap molecules of the substance but allow solvent molecules to pass out.

The change may comprise a chemical change. A first solution may be passed into the biocapsule, then a second solution gassed into the biocapsule which reacts with the first solution to yield the substance in the biocapsule in such manner as to remain encapsulated.

The first and second solutions may comprise different solutes, or different solvents, or both.

Liquid ammonia, such as has been proposed for water-insoluble substances as noted above, is found now also to be useful for certain water-soluble substances which, however, cannot be encapsulated from aqueous solution for the reason stated above. It is especially suitable for use with some acids and in particular with amino acids.

Amino acids may be in the salt form, preferably the ammonium salt, and may be encapsulated alone or together with other ingredients, for example fish oils. In addition to increasing the nutritional value of such capsules, fish oils also protect the amino acids from leaching out of the capsules. For example, the amino acid histidine may be encapsulated as follows:

Histidine (L-α-amino-B-imidazolepropionic acid) 5 g,iis dissolved in liquid ammonia 150 g. Yeast 25 g, is added slowly with continuous stirring. After 5 minutes the mixture is poured into absolute ethanol 600 ml and the resultant mixture filtered and washed with absolute ethanol under gentle suction. The filter cake is spread out and allowed to dry in air.

Analysis revealed approximately 12% w/w of histidine encapsulated by the yeast after this process was carried out.

Materials encapsulated in starch or yeast granules, for example, may be used as animal feeds, in particular for ruminant feeds where the capsule coating would protect its contents, ie. amino acids, during passage through the first stomach (rumen), where normally they would be destroyed, until they entered the second stomach (abomasum) where they may be absorbed intact.

In addition, such capsules may be used as feed for fish larvae, and the content of the capsules could be tailored specifically for the particular needs of each stage of the growing larvae.

Many other substances may be encapsulated, for example:

Enzymes could be encapsulated to be put in or on materials needing some degree of digestion, for example, in washing powders;

Perfumes optical brighteners may be encapsulated in spray starches;

Biocidal agents, for example insecticides, may be encapsulated and used in a dust form rather than the commonly used pellets, i.e. metaldehyde pellets for killing slugs, to prevent ingestion by other animals such as birds;

Plant fertilisers may be encapsulated, the rate of release being regulated by the type of capsule coating used;

Intumescent flame retardant, i.e. two or more different reactive compounds which produce an expanded flame retardant, may be encapsulated separately;

Oil may be encapsulated in carbohydrate capsules in a proportion such that addition of a fixed amount of water produces a pastry for baking, while other proportions may produce cake mixes and the like.

It will be appreciated that it is not intended to limit the invention to the above examples only, many variations, such as might readily occur to one skilled in the art, being possible, without departing from the scope thereof.

We claim:

1. A method for encapsulating a water-soluble substance in a biocapsule comprising passing a solution into the biocapsule, then effecting a change in the biocapsule/solution system such that the water-soluble substance remains encapsulated while a solvent comprising liquid ammonia escapes.

2. A method according to claim 1, in which the change comprises a physical change.

3. A method according to claim 2, in which the physical change involves an increase in solution concentration within the capsule.

4. A method according to claim 2, in which the physical change involves a decrease in solubility of the substance in the solution within the capsule.

5. A method according to claim 3, in which the substance precipitates from a saturated solution.

6. A method according to claim 2, in which the solvent evaporates from the capsule.

7. A method according to claim 2, in which the solution swells the bio-capsule and the physical change comprises a reversal of the swelling sufficient to trap molecules of the substance but allow solvent molecules to pass.

8. A method according to claim 1, in which the substance is dissolved in liquid ammonia.

9. A method according to claim 8, in which the biocapsule/solution system warms to a temperature at which liquid ammonia evaporates.

10. A method according to claim 1, in which the change comprises a chemical change.

11. A method according to claim 10, in which a first solution is passed into the biocapsule, then a second solution is passed into the biocapsule which reacts with the first solution to yield the substance in the biocapsule in such manner as to remain encapsulated.

12. A method according to claim 11, in which the first and second solutions comprise different solutes.

13. A method according to claim 11, in which the first and second solutions comprise different solvents.

14. A method for encapsulating a water-soluble substance in a biocapsule comprising dissolving the water-soluble substance in liquid ammonia to form a solution of the water-soluble substance and liquid ammonia, passing the solution into the biocapsule and removing the liquid ammonia such that the water-soluble substance remains encapsulated in the biocapsule.

15. A method according to claim 14, in which the water-soluble substance comprises an acid.

16. A method according to claim 15, in which the water-soluble substance comprises an amino acid.

17. A method according to claim 16, wherein the amino acid is histidine.

18. A method according to claim 14 in which the biocapsule is a yeast cell.

19. A method according to claim 14 in which the solution contains fish oils.

* * * * *